US011640851B2

(12) United States Patent
Hanson

(10) Patent No.: US 11,640,851 B2
(45) Date of Patent: May 2, 2023

(54) COMPUTATIONAL REDUCTION VACCINE FOR COVID-19 BIN75

(71) Applicant: Matthew Vernon Hanson, Cambridge, MA (US)

(72) Inventor: Matthew Vernon Hanson, Cambridge, MA (US)

( * ) Notice: Subject to any disclaimer, the term of this patent is extended or adjusted under 35 U.S.C. 154(b) by 154 days.

(21) Appl. No.: 17/139,287

(22) Filed: Dec. 31, 2020

(65) Prior Publication Data

US 2021/0407626 A1 Dec. 30, 2021

Related U.S. Application Data

(60) Provisional application No. 63/045,121, filed on Jun. 28, 2020.

(51) Int. Cl.

| | |
|---|---|
| ***A61K 39/12*** | (2006.01) |
| ***A61K 39/215*** | (2006.01) |
| ***C12N 1/08*** | (2006.01) |
| ***C12N 7/04*** | (2006.01) |
| ***G16B 50/00*** | (2019.01) |
| ***G16B 35/10*** | (2019.01) |
| ***A61K 39/00*** | (2006.01) |

(52) U.S. Cl.
CPC .............. *G16B 50/00* (2019.02); *A61K 39/00* (2013.01); *A61K 39/215* (2013.01); *G16B 35/10* (2019.02); *A61K 39/12* (2013.01); *C12N 1/08* (2013.01); *C12N 7/04* (2013.01); *C12N 2770/20034* (2013.01)

(58) Field of Classification Search
None
See application file for complete search history.

(56) References Cited

PUBLICATIONS

Gen Bank Accession No. MT607247.1 (first seen at NCBI on Jun. 15, 2020) (Year: 2020).*

* cited by examiner

*Primary Examiner* — Nicole Kinsey White

(57) ABSTRACT

A vaccine candidate is herein described comprised by statistically significant DNA fragments resulting in three types of compositions: 1) a composition of statistically significant DNA fragments, 2) a composition of RNA transcripts corresponding to the statistically significant DNA fragments, and 3) a computational reduction composition wherein the DNA fragments are fully or partially subtracted from a base organism, resulting in a synthetic organism which has a high statistical likelihood of problematic functions being partially or fully removed.

3 Claims, 3 Drawing Sheets

Specification includes a Sequence Listing.

| SEQ ID | Bin | Appearances | Appearances % | RecordID | Strip | Location |
|---|---|---|---|---|---|---|
| SEQ ID NO: 1 | Bin075 | 3929 | 0.997714576 | MT259284.1 | TCTTAAAGATGGCACTTGTGGCTTAGTAGAAGTTGAAAAAGGCGTTTTGCCTCAACTTGAACAGCCCTATGTGTTCATCAA | 400 to 481 |
| SEQ ID NO: 2 | Bin075 | 3928 | 0.99746064 | MT365025.1 | GTATGATTTCGGTGATTTCATACAAACCACGCCAGGTAGTGGAGTTCCTGTTGTAGATTCTTATTATTCATTGTTA | 14088 to 14164 |
| SEQ ID NO: 3 | Bin075 | 3926 | 0.996952768 | MT365025.1 | AAATGGCTTATAGGTTTAATGGTATTGGAGTTACACAGAATGTTCTCTATGAGAACCAAAAATTGATTGCCAACCAATTTAATAGT | 24264 to 24350 |
| SEQ ID NO: 4 | Bin075 | 3926 | 0.996952768 | MT365025.1 | CAACATCTTAAAGATGGCACTTGTGGCTTAGTAGAAGTTGAAAAAGGCGTTTTGCCTCAACTTGAACAGCCCTATGTGTTCATCAA | 395 to 481 |
| SEQ ID NO: 5 | Bin075 | 3920 | 0.995429152 | MT365025.1 | GAACCACCTTGTAGGTTTGTTACAGACACACCTAAAGGTCCTAAAGTGAAGTATTTATACTTTATTAAAGGATTAAACAACCTAAATAGAGGTATG | 12893 to 12989 |
| SEQ ID NO: 6 | Bin075 | 3917 | 0.994667344 | MT470125.1 | TTCATCTAAGTGTGTGTGTTCTGTTATTGATTTATTACTTGATGATTTTGTTGAAATAATAAAATCCCAAGATTTATCTGTAGTTTCTAAGGTT | 20478 to 20572 |
| SEQ ID NO: 7 | Bin075 | 3916 | 0.994413408 | MT365025.1 | AGGGTGGTCGCACTATTGCCTTTGGAGGCTGTGTGTTCTCTTATGTTGGTTGCCATAACAAGTGTGCCTATTGGGTTCC | 1461 to 1540 |
| SEQ ID NO: 8 | Bin075 | 3912 | 0.993397664 | MT539163.1 | TTGTTGCGGCAATAGTGTTTATAACACTTTGCTTCACACTCAAAAGAAAGACAGAATGATTGAACTTTCATTAAT | 27701 to 27776 |
| SEQ ID NO: 9 | Bin075 | 3908 | 0.99238192 | MT612198.1 | TTTAATTGTTACTTTCCTTTACAATCATATGGTTTCCAACCCACTAATGGTGTTGGTTACCAACCATACAGAGTAGTA | 23018 to 23096 |
| SEQ ID NO: 10 | Bin075 | 3904 | 0.991366176 | MT461654.1 | AGGTTTTAATTGTTACTTTCCTTTACAATCATATGGTTTCCAACCCACTAATGGTGTTGGTTACCAACCATACAGAGTAGTA | 23014 to 23096 |
| SEQ ID NO: 11 | Bin075 | 3902 | 0.990858304 | MT451733.1 | ACACCTTGTAATGGTGTTGAAGGTTTTAATTGTTACTTTCCTTTACAATCATATGGTTTCCAACCCACTAATGGTGTTGGTTACCAAC | 22994 to 23082 |
| SEQ ID NO: 12 | Bin075 | 3899 | 0.990096496 | MT576689.1 | ACAAGAGGAAGTTCAAGAACTTTACTCTCCAATTTTTCTTATTGTTGCGGCAATAGTGTTTATAACACTTTGCTTCACACTCAAAAGAAAG | 27660 to 27751 |
| SEQ ID NO: 13 | Bin075 | 3886 | 0.986795328 | MT358637.1 | ACCGAAGTTGTAGGAGACATTATACTTAAACCAGCAAATAATAGTTTAAAAATTACAGAAGAGGTTGGCCACACA | 6470 to 6545 |
| SEQ ID NO: 14 | Bin075 | 3883 | 0.98603352 | MT365025.1 | TCTTGAGTGTAATGTGAAAACTACCGAAGTTGTAGGAGACATTATACTTAAACCAGCAAATAATAGTTTAAAAATTACAGAAGAGGTTGGCCACACA | 6448 to 6545 |
| SEQ ID NO: 15 | Bin075 | 3883 | 0.98603352 | MT459838.1 | TTAGGGAATTTGTGTTTAAGAATATTGATGGTTATTTTAAAATATATTCTAAGCACACGCCTATTAATTTAGTGCGT | 22128 to 22205 |
| SEQ ID NO: 16 | Bin075 | 3882 | 0.985779584 | MT365025.1 | CAACCAACAGAATCTATTGTTAGATTTCCTAATATTACAAACTTGTGCCCTTTTGGTGAAGTTTTTAACGCCACCAGATT | 22523 to 22603 |
| SEQ ID NO: 17 | Bin075 | 3868 | 0.982224479 | MT365025.1 | CTCTAAAAGCCCCAAAAGAAATTATCTTCTTAGAGGGAGAAACACTTCCCACAGAAGTGTTAACAGAGGAAGTTGTCTTGAAA | 2460 to 2543 |
| SEQ ID NO: 18 | Bin075 | 2620 | 0.665312341 | MT509463.1 | TGGTGAGTTTAAATTGGCTTCACATATGTATTGTTCTTTTTACCCTCCAGATGAGGATGAAGAAGAAGGTGATTGTGAAGAAGAAGAGTTTGAGCC | 2998 to 3094 |

Figure 1

COMPUTATIONAL REDUCTION VACCINE FOR COVID-19 BIN75

BACKGROUND OF THE INVENTION

The present invention focuses on a computational reduction vaccine for Covid-19 with reduction fragments between 75 and 99 base pairs.

A computational reduction vaccine may be defined herein as a vaccine candidate which is arrived at by removing various non-repetitive fragments in a virus or bacteria first computationally, then via Crispr in a "Super-Organism" (an organism which contains all, or the majority, of those fragments), and then utilizing the remaining organism as a traditional "live" or "dead" vaccine, which even though marginally computationally reduced, is still recognizable by the human immune system as an invader and therefore provokes a useful immune response. That immune response then shields the recipient from the actual virus going forward.

It is now possible via Python modules such as Numpy (numerical Python) and Biopython (a module specifically designed for computationally manipulating DNA sequences), to analyze in great detail and with great speed thousands, or even millions of sequence records available through the NIH GenBank databases.

Those computational methods are not herein described, but the statistical analysis below will illustrate the efficacy of the method in determining the frequency of various structures, as well as the ability to track those structures though time. It is along those two lines—frequency of appearance, and consistency of appearance, across an entire genetic database that one can derive vaccine candidates computationally.

The traditional way to do this would be to remove each fragment or structure via Crispr one by one and test the resulting organism for problematic function. Once problematic function was discovered, use the resulting live or dead virus could be used as a vaccine. However, in the case of Covid-19, where solutions are demanded in shorter time frames, it is more efficient to simply remove all potential problematic function fragments via various fragment length groups in order to create one or two potential vaccine candidates instead of hundreds. This is the second of two such vaccines.

BRIEF DESCRIPTION OF SEVERAL VIEWS OF THE DRAWINGS

FIG. 1 is a table of computational fragment reductions from Covid-19 which are between 75 and 99 base pairs. From left to right, you have the SEQ ID indicating the sequence ID in the sequence file; "Bin" size, or size of the fragments; the number of appearances of the fragment across the entire Covid-19 database; the appearance percent of the fragment expressed as a decimal; the Record ID for the reference organism in which the fragment was first found; the "strip" or fragment which when removed from a Covid-19 Super Organism or Base Organism will give us a vaccine; and the location of the fragment in the "Base Organism" file SEQ ID NO: 38.

DETAILED DESCRIPTION OF THE INVENTION

Figure 2:
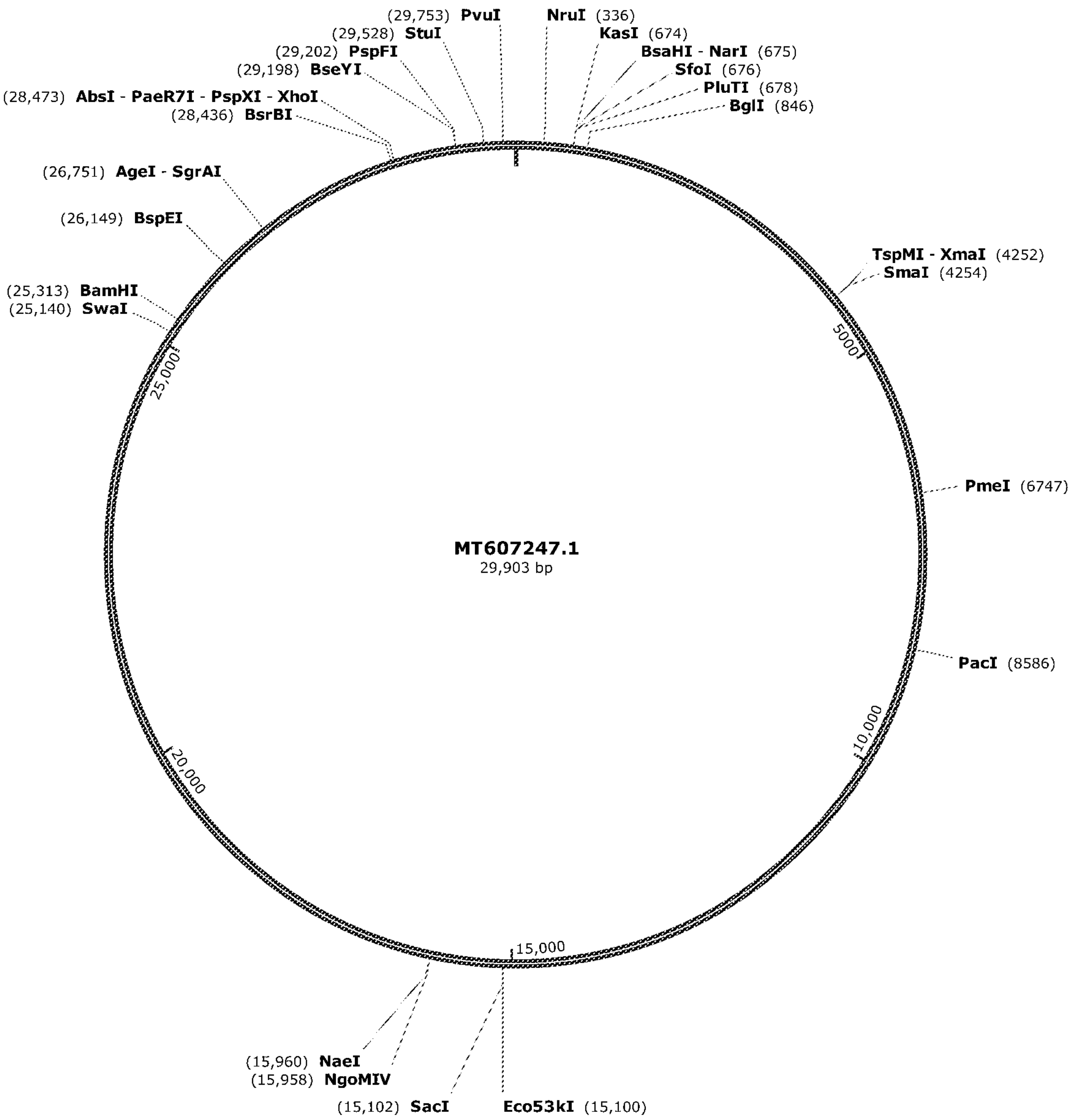
FIG. 2 is a SnapGene circular view of Covid-19 sample MT607247.1 from which this vaccine is derived.
Figure 3:
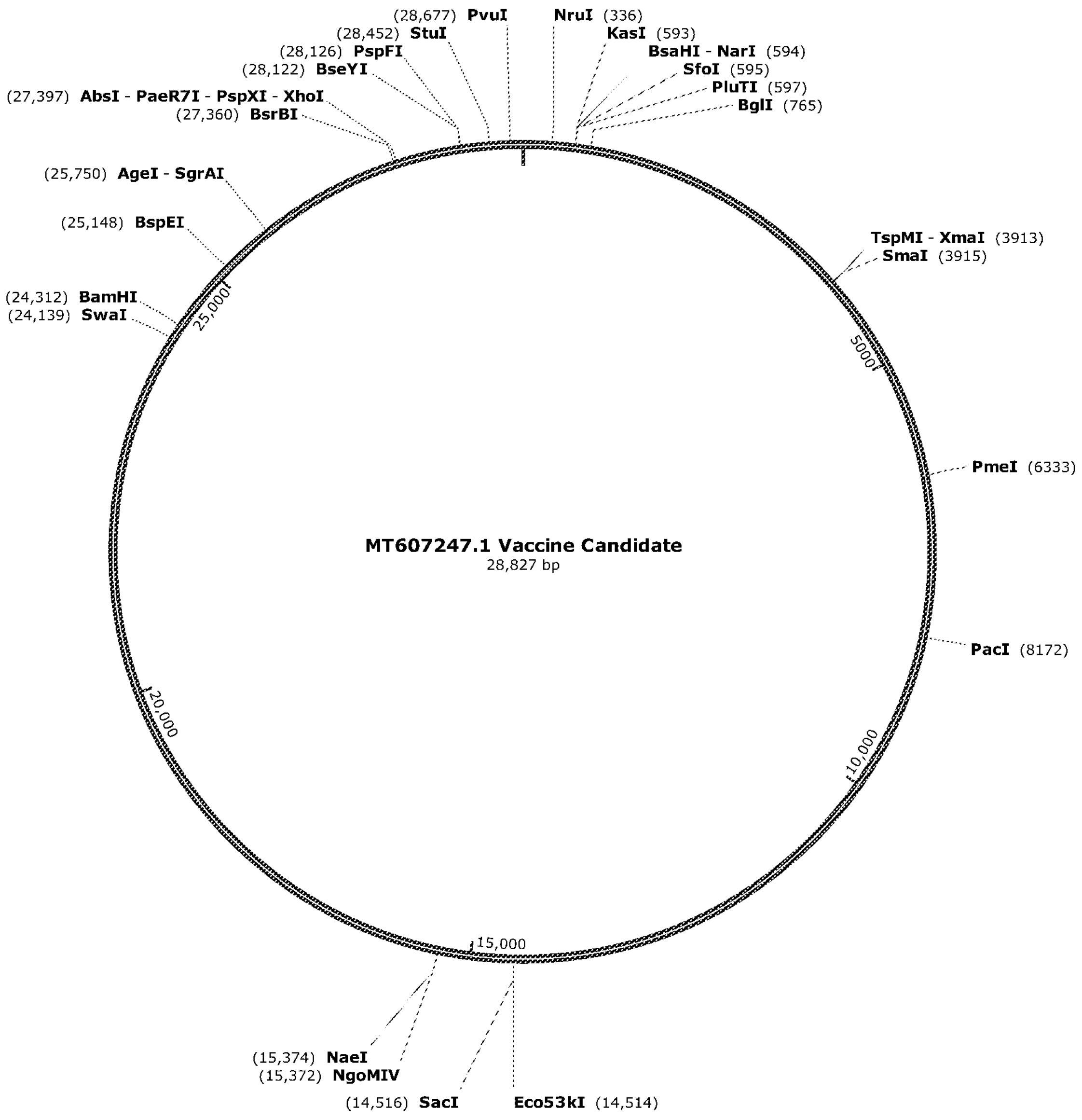
FIG. 3 is the same SnapGene circular view of MT607247.1 with the fragments removed.

There are several types of vaccines. This invention introduces a new type of vaccine which is a computationally derived reductive vaccine. A computationally derived reductive vaccine utilizes statistical computation to arrive at a list of fragments which can then be removed from live viruses or bacteria via Crispr to arrive at "neutered" versions which can then form the basis for the vaccine.

Computational reduction in this case may be defined as non-laboratory computational reduction of organisms into fragments, which then can be assessed on the basis of frequency across an entire range of similar organisms as well as computationally tested to confirm that those structures are unique to the virus or bacteria in question. The particulars of the method of discovery for these fragments is proprietary.

What is not proprietary is the statistical analysis of the fragments which are outlined in FIG. 1 and below. In the case of this particular vaccine candidate, the fragments which are included are between 75 and 99 base-pairs and appear in the NIH Covid-19 database greater than 66% of the time. The Covid-19 database "snapshot" from which the fragments in this patent were selected was taken on Jun. 16, 2020 at 5:21 am. That database is available upon request.

The result of this patent is relatively simple. When a "Super Organism" or Covid-19 sample which contains all, or most, of the fragments outlined below is found, that Super Organism can then be genetically modified in a laboratory using Crispr to remove those fragments. Once all those fragments are removed from the organism, it can then be tested to see if problematic function remains. "Problematic function" in the case of Covid-19 is two-fold: functions of the virus which cause high transmissibility rates, and functions of the virus which cause high mortality rates. It may take us years to figure out exactly what those functions are and where they appear exactly on the genetic assay. This patent provides a shortcut by simply removing all of the most likely candidates for those problematic functions by identifying fragments which appear often enough not to be considered mutations (i.e. fragments only appearing in one or two samples).

The scan of the entire database of Covid-19 provides 18 fragments between 75 and 99 base pairs which appear more than 66% of the time across the entire database. These fragments are unique to Covid-19 and cannot be found in any other virus in the NIH GenBank databases.

In creation of the vaccine candidate we can also view that vaccine not only as a reductive entity (a library of removable fragments) which can be manufactured from a variety of possible starting organisms, but also as a complete organism which has potentially been "neutered" of its destructive features.

In order to arrive at that possibility, we must first find a Covid-19 sample which contains all of these structures. Of the 3,938 complete Covid-19 sequences in the Jun. 16, 2020 Covid-19 database, 2,417 contain all 18 fragments. When computationally reduced, some fragments overlap, meaning those 2,417 samples which contain the fragments also had a maximum removal rate of 13 of 18 fragments.

So to create a reductive vaccine, computationally those fragments are removed to create the vaccine candidate as shown in SEQ ID NO: 37. The original reference sequence can be downloaded from NIH via the reference MT607247.1. As previously stated, there are also 2,417 other reference candidates which could be used as Super Organisms or Base Organisms for the next generation of vaccines. That list is available upon request.

This application also seeks to cover the RNA transcript of each of the fragments. (SEQ ID. NOs: 19-36). It may well be that RNA transcript vaccines based on these fragments would be of equal or greater efficacy in triggering a useful immune response.

It should also be noted that these fragments are 75 base pairs or greater, which means a fragment has only a 1 in 1.60 quattuordecillion ($4^{75}$) chance of occurring—in the entire history of the planet. In other words, even at a 66% recurrence rate across the entire Covid-19 genome, these fragments represent viable mathematical targets for vaccines.

This application identifies 18 such fragments.

Having described my invention herein, I claim:

1. A composition comprised of statistically significant DNA fragments consisting of the sequences of SEQ ID NOs: 1-18 encapsulated in an appropriate delivery system.

2. A composition comprised of statistically significant mRNA fragments consisting of the sequences of SEQ ID NOs: 19-36 encapsulated in an appropriate delivery system.

3. A composition comprising a SARS-CoV-2 particle comprising the genome represented by SEQ ID NO: 37, where one or more of SEQ ID NOs: 1-18 have been removed from the genome.

* * * * *

SEQUENCE LISTING

```
<160> NUMBER OF SEQ ID NOS: 37

<210> SEQ ID NO 1
<211> LENGTH: 81
<212> TYPE: DNA
<213> ORGANISM: Artificial Sequence
<220> FEATURE:
<223> OTHER INFORMATION: SEQ ID NOs 1-18 are DNA fragments found in a
      wide variety of Covid-19 samples (see Specification). This
      fragment was originally scanned from NIH ID: MT259284.1.

<400> SEQUENCE: 1

tcttaaagat ggcacttgtg gcttagtaga agttgaaaaa ggcgttttgc ctcaacttga     60

acagccctat gtgttcatca a                                               81


<210> SEQ ID NO 2
<211> LENGTH: 76
<212> TYPE: DNA
<213> ORGANISM: Artificial Sequence
<220> FEATURE:
<223> OTHER INFORMATION: SEQ ID NOs 1-18 are DNA fragments found in a
      wide variety of Covid-19 samples (see Specification). This
      fragment was originally scanned from NIH ID: MT365025.1

<400> SEQUENCE: 2

gtatgatttc ggtgatttca tacaaaccac gccaggtagt ggagttcctg ttgtagattc     60

ttattattca ttgtta                                                     76


<210> SEQ ID NO 3
<211> LENGTH: 86
<212> TYPE: DNA
<213> ORGANISM: Artificial Sequence
<220> FEATURE:
<223> OTHER INFORMATION: SEQ ID NOs 1-18 are DNA fragments found in a
      wide variety of Covid-19 samples (see Specification). This
      fragment was originally scanned from NIH ID: MT365025.1

<400> SEQUENCE: 3

aaatggctta taggtttaat ggtattggag ttacacagaa tgttctctat gagaaccaaa     60

aattgattgc caaccaattt aatagt                                          86


<210> SEQ ID NO 4
<211> LENGTH: 86
<212> TYPE: DNA
<213> ORGANISM: Artificial Sequence
<220> FEATURE:
<223> OTHER INFORMATION: SEQ ID NOs 1-18 are DNA fragments found in a
      wide variety of Covid-19 samples (see Specification). This
      fragment was originally scanned from NIH ID: MT365025.1

<400> SEQUENCE: 4

caacatctta aagatggcac ttgtggctta gtagaagttg aaaaaggcgt tttgcctcaa     60

cttgaacagc cctatgtgtt catcaa                                          86


<210> SEQ ID NO 5
<211> LENGTH: 96
```

-continued

<212> TYPE: DNA
<213> ORGANISM: Artificial Sequence
<220> FEATURE:
<223> OTHER INFORMATION: SEQ ID NOs 1-18 are DNA fragments found in a wide variety of Covid-19 samples (see Specification). This fragment was originally scanned from NIH ID: MT365025.1

<400> SEQUENCE: 5
gaaccacctt gtaggtttgt tacagacaca cctaaaggtc ctaaagtgaa gtatttatac 60
tttattaaag gattaaacaa cctaaataga ggtatg 96

<210> SEQ ID NO 6
<211> LENGTH: 94
<212> TYPE: DNA
<213> ORGANISM: Artificial Sequence
<220> FEATURE:
<223> OTHER INFORMATION: SEQ ID NOs 1-18 are DNA fragments found in a wide variety of Covid-19 samples (see Specification). This fragment was originally scanned from NIH ID: MT470125.1

<400> SEQUENCE: 6
ttcatctaag tgtgtgtgtt ctgttattga tttattactt gatgattttg ttgaaataat 60
aaaatcccaa gatttatctg tagtttctaa ggtt 94

<210> SEQ ID NO 7
<211> LENGTH: 79
<212> TYPE: DNA
<213> ORGANISM: Artificial Sequence
<220> FEATURE:
<223> OTHER INFORMATION: SEQ ID NOs 1-18 are DNA fragments found in a wide variety of Covid-19 samples (see Specification). This fragment was originally scanned from NIH ID: MT365025.1

<400> SEQUENCE: 7
agggtggtcg cactattgcc tttggaggct gtgtgttctc ttatgttggt tgccataaca 60
agtgtgccta ttgggttcc 79

<210> SEQ ID NO 8
<211> LENGTH: 75
<212> TYPE: DNA
<213> ORGANISM: Artificial Sequence
<220> FEATURE:
<223> OTHER INFORMATION: SEQ ID NOs 1-18 are DNA fragments found in a wide variety of Covid-19 samples (see Specification). This fragment was originally scanned from NIH ID: MT539163.1

<400> SEQUENCE: 8
ttgttgcggc aatagtgttt ataacacttt gcttcacact caaaagaaag acagaatgat 60
tgaactttca ttaat 75

<210> SEQ ID NO 9
<211> LENGTH: 78
<212> TYPE: DNA
<213> ORGANISM: Artificial Sequence
<220> FEATURE:
<223> OTHER INFORMATION: SEQ ID NOs 1-18 are DNA fragments found in a wide variety of Covid-19 samples (see Specification). This fragment was originally scanned from NIH ID: MT612198.1

<400> SEQUENCE: 9
tttaattgtt actttccttt acaatcatat ggtttccaac ccactaatgg tgttggttac 60
caaccataca gagtagta 78

<210> SEQ ID NO 10

-continued

<211> LENGTH: 82
<212> TYPE: DNA
<213> ORGANISM: Artificial Sequence
<220> FEATURE:
<223> OTHER INFORMATION: SEQ ID NOs 1-18 are DNA fragments found in a wide variety of Covid-19 samples (see Specification). This fragment was originally scanned from NIH ID: MT461654.1

<400> SEQUENCE: 10
aggttttaat tgttactttc ctttacaatc atatggtttc caacccacta atggtgttgg 60
ttaccaacca tacagagtag ta 82

<210> SEQ ID NO 11
<211> LENGTH: 88
<212> TYPE: DNA
<213> ORGANISM: Artificial Sequence
<220> FEATURE:
<223> OTHER INFORMATION: SEQ ID NOs 1-18 are DNA fragments found in a wide variety of Covid-19 samples (see Specification). This fragment was originally scanned from NIH ID: MT451733.1

<400> SEQUENCE: 11
acaccttgta atggtgttga aggttttaat tgttactttc ctttacaatc atatggtttc 60
caacccacta atggtgttgg ttaccaac 88

<210> SEQ ID NO 12
<211> LENGTH: 91
<212> TYPE: DNA
<213> ORGANISM: Artificial Sequence
<220> FEATURE:
<223> OTHER INFORMATION: SEQ ID NOs 1-18 are DNA fragments found in a wide variety of Covid-19 samples (see Specification). This fragment was originally scanned from NIH ID: MT576689.1

<400> SEQUENCE: 12
acaagaggaa gttcaagaac tttactctcc aatttttctt attgttgcgg caatagtgtt 60
tataacactt tgcttcacac tcaaaagaaa g 91

<210> SEQ ID NO 13
<211> LENGTH: 75
<212> TYPE: DNA
<213> ORGANISM: Artificial Sequence
<220> FEATURE:
<223> OTHER INFORMATION: SEQ ID NOs 1-18 are DNA fragments found in a wide variety of Covid-19 samples (see Specification). This fragment was originally scanned from NIH ID: MT358637.1

<400> SEQUENCE: 13
accgaagttg taggagacat tatacttaaa ccagcaaata atagtttaaa aattacagaa 60
gaggttggcc acaca 75

<210> SEQ ID NO 14
<211> LENGTH: 97
<212> TYPE: DNA
<213> ORGANISM: Artificial Sequence
<220> FEATURE:
<223> OTHER INFORMATION: SEQ ID NOs 1-18 are DNA fragments found in a wide variety of Covid-19 samples (see Specification). This fragment was originally scanned from NIH ID: MT365025.1

<400> SEQUENCE: 14
tcttgagtgt aatgtgaaaa ctaccgaagt tgtaggagac attatactta aaccagcaaa 60
taatagttta aaaattacag aagaggttgg ccacaca 97

-continued

<210> SEQ ID NO 15
<211> LENGTH: 77
<212> TYPE: DNA
<213> ORGANISM: Artificial Sequence
<220> FEATURE:
<223> OTHER INFORMATION: SEQ ID NOs 1-18 are DNA fragments found in a wide variety of Covid-19 samples (see Specification). This fragment was originally scanned from NIH ID: MT459838.1

<400> SEQUENCE: 15
ttagggaatt tgtgtttaag aatattgatg gttattttaa aatatattct aagcacacgc 60
ctattaattt agtgcgt 77

<210> SEQ ID NO 16
<211> LENGTH: 80
<212> TYPE: DNA
<213> ORGANISM: Artificial Sequence
<220> FEATURE:
<223> OTHER INFORMATION: SEQ ID NOs 1-18 are DNA fragments found in a wide variety of Covid-19 samples (see Specification). This fragment was originally scanned from NIH ID: MT365025.1

<400> SEQUENCE: 16
caaccaacag aatctattgt tagatttcct aatattacaa acttgtgccc ttttggtgaa 60
gtttttaacg ccaccagatt 80

<210> SEQ ID NO 17
<211> LENGTH: 83
<212> TYPE: DNA
<213> ORGANISM: Artificial Sequence
<220> FEATURE:
<223> OTHER INFORMATION: SEQ ID NOs 1-18 are DNA fragments found in a wide variety of Covid-19 samples (see Specification). This fragment was originally scanned from NIH ID: MT365025.1

<400> SEQUENCE: 17
ctctaaaagc cccaaaagaa attatcttct tagagggaga aacacttccc acagaagtgt 60
taacagagga agttgtcttg aaa 83

<210> SEQ ID NO 18
<211> LENGTH: 96
<212> TYPE: DNA
<213> ORGANISM: Artificial Sequence
<220> FEATURE:
<223> OTHER INFORMATION: SEQ ID NOs 1-18 are DNA fragments found in a wide variety of Covid-19 samples (see Specification). This fragment was originally scanned from NIH ID: MT509463.1

<400> SEQUENCE: 18
tggtgagttt aaattggctt cacatatgta ttgttctttt taccctccag atgaggatga 60
agaagaaggt gattgtgaag aagaagagtt tgagcc 96

<210> SEQ ID NO 19
<211> LENGTH: 81
<212> TYPE: RNA
<213> ORGANISM: Artificial Sequence
<220> FEATURE:
<223> OTHER INFORMATION: SEQ ID NOs 19-36 are the mRNA transcriptions of SEQ ID NOs 1-18.

<400> SEQUENCE: 19
ucuuaaagau ggcacuugug gcuuaguaga aguugaaaaa ggcguuuugc cucaacuuga 60
acagcccuau guguucauca a 81

<210> SEQ ID NO 20
<211> LENGTH: 76
<212> TYPE: RNA
<213> ORGANISM: Artificial Sequence
<220> FEATURE:
<223> OTHER INFORMATION: SEQ ID NOs 19-36 are the mRNA transcriptions of SEQ ID NOs 1-18.

<400> SEQUENCE: 20
guaugauuuc ggugauuuca uacaaaccac gccagguagu ggaguuccug uuguagauuc 60
uuauuauuca uuguua 76

<210> SEQ ID NO 21
<211> LENGTH: 86
<212> TYPE: RNA
<213> ORGANISM: Artificial Sequence
<220> FEATURE:
<223> OTHER INFORMATION: SEQ ID NOs 19-36 are the mRNA transcriptions of SEQ ID NOs 1-18.

<400> SEQUENCE: 21
aaauggcuua uagguuuaau gguauuggag uuacacagaa uguucucuau gagaaccaaa 60
aauugauugc caaccaauuu aauagu 86

<210> SEQ ID NO 22
<211> LENGTH: 86
<212> TYPE: RNA
<213> ORGANISM: Artificial Sequence
<220> FEATURE:
<223> OTHER INFORMATION: SEQ ID NOs 19-36 are the mRNA transcriptions of SEQ ID NOs 1-18.

<400> SEQUENCE: 22
caacaucuua aagauggcac uuguggcuua guagaaguug aaaaaggcgu uuugccucaa 60
cuugaacagc ccuauguguu caucaa 86

<210> SEQ ID NO 23
<211> LENGTH: 96
<212> TYPE: RNA
<213> ORGANISM: Artificial Sequence
<220> FEATURE:
<223> OTHER INFORMATION: SEQ ID NOs 19-36 are the mRNA transcriptions of SEQ ID NOs 1-18.

<400> SEQUENCE: 23
gaaccaccuu guagguuugu uacagacaca ccuaaaggu cuaaagugaa guauuuauac 60
uuuauuaaag gauuaaacaa ccuaaauaga gguaug 96

<210> SEQ ID NO 24
<211> LENGTH: 94
<212> TYPE: RNA
<213> ORGANISM: Artificial Sequence
<220> FEATURE:
<223> OTHER INFORMATION: SEQ ID NOs 19-36 are the mRNA transcriptions of SEQ ID NOs 1-18.

<400> SEQUENCE: 24
uucaucuaag uguguguguu cuguuauuga uuuauuacuu gaugauuuug uugaaauaau 60
aaaaucccaa gauuuaucug uaguuucuaa gguu 94

<210> SEQ ID NO 25
<211> LENGTH: 79
<212> TYPE: RNA
<213> ORGANISM: Artificial Sequence
<220> FEATURE:
<223> OTHER INFORMATION: SEQ ID NOs 19-36 are the mRNA transcriptions of SEQ ID NOs 1-18.

<400> SEQUENCE: 25 agggugg ucg cacuauugcc uuuggaggcu guguguucuc uuauguuggu ugccauaaca 60
agugugccua uuggguucc 79

<210> SEQ ID NO 26
<211> LENGTH: 75
<212> TYPE: RNA
<213> ORGANISM: Artificial Sequence
<220> FEATURE:
<223> OTHER INFORMATION: SEQ ID NOs 19-36 are the mRNA transcriptions of SEQ ID NOs 1-18.

<400> SEQUENCE: 26
uuguugcggc aauaguguuu auaacacuuu gcuucacacu caaaagaaag acagaaugau 60
ugaacuuuca uuaau 75

<210> SEQ ID NO 27
<211> LENGTH: 78
<212> TYPE: RNA
<213> ORGANISM: Artificial Sequence
<220> FEATURE:
<223> OTHER INFORMATION: SEQ ID NOs 19-36 are the mRNA transcriptions of SEQ ID NOs 1-18.

<400> SEQUENCE: 27
uuuaauuguu acuuuccuuu acaaucauau gguuuccaac ccacuaaugg uguugguuac 60
caaccauaca gaguagua 78

<210> SEQ ID NO 28
<211> LENGTH: 82
<212> TYPE: RNA
<213> ORGANISM: Artificial Sequence
<220> FEATURE:
<223> OTHER INFORMATION: SEQ ID NOs 19-36 are the mRNA transcriptions of SEQ ID NOs 1-18.

<400> SEQUENCE: 28
agguuuuaau uguuacuuuc cuuuacaauc auaugguuuc caacccacua augguguugg 60
uuaccaacca uacagaguag ua 82

<210> SEQ ID NO 29
<211> LENGTH: 88
<212> TYPE: RNA
<213> ORGANISM: Artificial Sequence
<220> FEATURE:
<223> OTHER INFORMATION: SEQ ID NOs 19-36 are the mRNA transcriptions of SEQ ID NOs 1-18.

<400> SEQUENCE: 29
acaccuugua augguguuga agguuuuaau uguuacuuuc cuuuacaauc auaugguuuc 60
caacccacua augguguugg uuaccaac 88

<210> SEQ ID NO 30
<211> LENGTH: 91
<212> TYPE: RNA
<213> ORGANISM: Artificial Sequence
<220> FEATURE:
<223> OTHER INFORMATION: SEQ ID NOs 19-36 are the mRNA transcriptions of SEQ ID NOs 1-18.

-continued

<400> SEQUENCE: 30
acaagaggaa guucaagaac uuuacucucc aauuuuucuu auuguugcgg caauaguguu 60
uauaacacuu ugcuucacac ucaaaagaaa g 91

<210> SEQ ID NO 31
<211> LENGTH: 75
<212> TYPE: RNA
<213> ORGANISM: Artificial Sequence
<220> FEATURE:
<223> OTHER INFORMATION: SEQ ID NOs 19-36 are the mRNA transcriptions of SEQ ID NOs 1-18.

<400> SEQUENCE: 31
accgaaguug uaggagacau uauacuuaaa ccagcaaaua auaguuuaaa aauuacagaa 60
gagguuggcc acaca 75

<210> SEQ ID NO 32
<211> LENGTH: 97
<212> TYPE: RNA
<213> ORGANISM: Artificial Sequence
<220> FEATURE:
<223> OTHER INFORMATION: SEQ ID NOs 19-36 are the mRNA transcriptions of SEQ ID NOs 1-18.

<400> SEQUENCE: 32
ucuugagugu aaugugaaaa cuaccgaagu uguaggagac auuauacuua aaccagcaaa 60
uaauaguuua aaaauuacag aagagguugg ccacaca 97

<210> SEQ ID NO 33
<211> LENGTH: 77
<212> TYPE: RNA
<213> ORGANISM: Artificial Sequence
<220> FEATURE:
<223> OTHER INFORMATION: SEQ ID NOs 19-36 are the mRNA transcriptions of SEQ ID NOs 1-18.

<400> SEQUENCE: 33
uuagggaauu uguguuuaag aauauugaug guuauuuuaa aauauauucu aagcacacgc 60
cuauuaauuu agugcgu 77

<210> SEQ ID NO 34
<211> LENGTH: 80
<212> TYPE: RNA
<213> ORGANISM: Artificial Sequence
<220> FEATURE:
<223> OTHER INFORMATION: SEQ ID NOs 19-36 are the mRNA transcriptions of SEQ ID NOs 1-18.

<400> SEQUENCE: 34
caaccaacag aaucuauugu uagauuuccu aauauuacaa acuugugccc uuuuggugaa 60
guuuuuaacg ccaccagauu 80

<210> SEQ ID NO 35
<211> LENGTH: 83
<212> TYPE: RNA
<213> ORGANISM: Artificial Sequence
<220> FEATURE:
<223> OTHER INFORMATION: SEQ ID NOs 19-36 are the mRNA transcriptions of SEQ ID NOs 1-18.

<400> SEQUENCE: 35
cucuaaaagc cccaaaagaa auuaucuucu uagagggaga aacacuuccc acagaagugu 60
uaacagagga aguugucuug aaa 83

<210> SEQ ID NO 36
<211> LENGTH: 96
<212> TYPE: RNA
<213> ORGANISM: Artificial Sequence
<220> FEATURE:
<223> OTHER INFORMATION: SEQ ID NOs 19-36 are the mRNA transcriptions of SEQ ID NOs 1-18.

<400> SEQUENCE: 36
uggugaguuu aaauuggcuu cacauaugua uuguucuuuu uacccuccag augaggauga 60
agaagaaggu gauugugaag aagaagaguu ugagcc 96

<210> SEQ ID NO 37
<211> LENGTH: 28827
<212> TYPE: DNA
<213> ORGANISM: Artificial Sequence
<220> FEATURE:
<223> OTHER INFORMATION: SEQ ID NO 37 is the “computational reduction vaccine candidate” per the Specification. The origin is MT607247.1 with SEQ ID NOs: 1-18 computationally removed.

<400> SEQUENCE: 37
attaaaggtt tataccttcc caggtaacaa accaaccaac tttcgatctc ttgtagatct 60
gttctctaaa cgaactttaa aatctgtgtg gctgtcactc ggctgcatgc ttagtgcact 120
cacgcagtat aattaataac taattactgt cgttgacagg acacgagtaa ctcgtctatc 180
ttctgcaggc tgcttacggt ttcgtccgtg ttgcagccga tcatcagcac atctaggttt 240
tgtccgggtg tgaccgaaag gtaagatgga gagccttgtc cctggtttca acgagaaaac 300
acacgtccaa ctcagtttgc ctgttttaca ggttcgcgac gtgctcgtac gtggctttgg 360
agactccgtg gaggaggtct tatcagaggc acgtcaacaa cgttcggatg ctcgaactgc 420
acctcatggt catgttatgg ttgagctggt agcagaactc gaaggcattc agtacggtcg 480
tagtggtgag acacttggtg tccttgtccc tcatgtgggc gaaataccag tggcttaccg 540
caaggttctt cttcgtaaga acggtaataa aggagctggt ggccatagtt acggcgccga 600
tctaaagtca tttgacttag gcgacgagct tggcactgat ccttatgaag attttcaaga 660
aaactggaac actaaacata gcagtggtgt tacccgtgaa ctcatgcgtg agcttaacgg 720
aggggcatac actcgctatg tcgataacaa cttctgtggc cctgatggct accctcttga 780
gtgcattaaa gaccttctag cacgtgctgg taaagcttca tgcactttgt ccgaacaact 840
ggactttatt gacactaaga ggggtgtata ctgctgccgt gaacatgagc atgaaattgc 900
ttggtacacg gaacgttctg aaaagagcta tgaattgcag acaccttttg aaattaaatt 960
ggcaaagaaa tttgacacct tcaatgggga atgtccaaat tttgtatttc ccttaaattc 1020
cataatcaag actattcaac caagggttga aaagaaaaag cttgatggct ttatgggtag 1080
aattcgatct gtctatccag ttgcgtcacc aaatgaatgc aaccaaatgt gcctttcaac 1140
tctcatgaag tgtgatcatt gtggtgaaac ttcatggcag acgggcgatt ttgttaaagc 1200
cacttgcgaa ttttgtggca ctgagaattt gactaaagaa ggtgccacta cttgtggtta 1260
cttaccccaa aatgctgttg ttaaaattta ttgtccagca tgtcacaatt cagaagtagg 1320
acctgagcat agtcttgccg aataccataa tgaatctggc ttgaaaacca ttcttcgtaa 1380
cgtgctagcg ctaacatagg ttgtaaccat acaggtgttg ttggagaagg ttccgaaggt 1440
cttaatgaca accttcttga aatactccaa aaagagaaag tcaacatcaa tattgttggt 1500

-continued

```
gactttaaac ttaatgaaga gatcgccatt attttggcat ctttttctgc ttccacaagt   1560
gcttttgtgg aaactgtgaa aggtttggat tataaagcat tcaaacaaat tgttgaatcc   1620
tgtggtaatt ttaaagttac aaaaggaaaa gctaaaaaag gtgcctggaa tattggtgaa   1680
cagaaatcaa tactgagtcc tctttatgca tttgcatcag aggctgctcg tgttgtacga   1740
tcaattttct cccgcactct tgaaactgct caaaattctg tgcgtgtttt acagaaggcc   1800
gctataacaa tactagatgg aatttcacag tattcactga gactcattga tgctatgatg   1860
ttcacatctg atttggctac taacaatcta gttgtaatgg cctacattac aggtggtgtt   1920
gttcagttga cttcgcagtg gctaactaac atctttggca ctgtttatga aaaactcaaa   1980
cccgtccttg attggcttga agagaagttt aaggaaggtg tagagtttct tagagacggt   2040
tgggaaattg ttaaatttat ctcaacctgt gcttgtgaaa ttgtcggtgg acaaattgtc   2100
acctgtgcaa aggaaattaa ggagagtgtt cagacattct ttaagcttgt aaataaattt   2160
ttggctttgt gtgctgactc tatcattatt ggtggagcta aacttaaagc cttgaattta   2220
ggtgaaacat ttgtcacgca ctcaaaggga ttgtacagaa agtgtgttaa atccagagaa   2280
gaaactggcc tactcatgca ctggtgattt acaaccatta gaacaaccta ctagtgaagc   2340
tgttgaagct ccattggttg gtacaccagt ttgtattaac gggcttatgt tgctcgaaat   2400
caaagacaca gaaaagtact gtgcccttgc acctaatatg atggtaacaa acaatacctt   2460
cacactcaaa ggcggtgcac caacaaaggt tacttttggt gatgacactg tgatagaagt   2520
gcaaggttac aagagtgtga atatcacttt tgaacttgat gaaaggattg ataaagtact   2580
taatgagaag tgctctgcct atacagttga actcggtaca gaagtaaatg agttcgcctg   2640
tgttgtggca gatgctgtca taaaaacttt gcaaccagta tctgaattac ttacaccact   2700
gggcattgat ttagatgagt ggagtatggc tacatactac ttatttgatg agtcatcaac   2760
tcaatatgag tatggtactg aagatgatta ccaaggtaaa cctttggaat ttggtgccac   2820
ttctgctgct cttcaacctg aagaagagca agaagaagat tggttagatg atgatagtca   2880
acaaactgtt ggtcaacaag acggcagtga ggacaatcag acaactacta ttcaaacaat   2940
tgttgaggtt caacctcaat tagagatgga acttacacca gttgttcaga ctattgaagt   3000
gaatagtttt agtggttatt taaaacttac tgacaatgta tacattaaaa atgcagacat   3060
tgtggaagaa gctaaaaagg taaaaccaac agtggttgtt aatgcagcca atgtttacct   3120
taaacatgga ggaggtgttg caggagcctt aaataaggct actaacaatg ccatgcaagt   3180
tgaatctgat gattacatag ctactaatgg accacttaaa gtgggtggta gttgtgtttt   3240
aagcggacac aatcttgcta aacactgtct tcatgttgtc ggcccaaatg ttaacaaagg   3300
tgaagacatt caacttctta agagtgctta tgaaaatttt aatcagcacg aagttctact   3360
tgcaccatta ttatcagctg gtatttttgg tgctgaccct atacattctt taagagtttg   3420
tgtagatact gttcgcacaa atgtctactt agctgtcttt gataaaaatc tctatgacaa   3480
acttgtttca agctttttgg aaatgaagag tgaaaagcaa gttgaacaaa agatcgctga   3540
gattcctaaa gaggaagtta agccatttat aactgaaagt aaaccttcag ttgaacagag   3600
aaaacaagat gataagaaaa tcaaagcttg tgttgaagaa gttacaacaa ctctggaaga   3660
aactaagttc ctcacagaaa acttgttact ttatattgac attaatggca atcttcatcc   3720
agattctgcc actcttgtta gtgacattga catcactttc ttaaagaaag atgctccata   3780
tatagtgggt gatgttgttc aagagggtgt tttaactgct gtggttatac ctactaaaaa   3840
ggctggtggc actactgaaa tgctagcgaa agctttgaga aaagtgccaa cagacaatta   3900
```

-continued

```
tataaccact tacccgggtc agggtttaaa tggttacact gtagaggagg caaagacagt   3960
gcttaaaaag tgtaaaagtg ccttttacat tctaccatct attatctcta atgagaagca   4020
agaaattctt ggaactgttt cttggaattt gcgagaaatg cttgcacatg cagaagaaac   4080
acgcaaatta atgcctgtct gtgtggaaac taaagccata gtttcaacta tacagcgtaa   4140
atataagggt attaaaatac aagagggtgt ggttgattat ggtgctagat tttactttta   4200
caccagtaaa acaactgtag cgtcacttat caacacactt aacgatctaa atgaaactct   4260
tgttacaatg ccacttggct atgtaacaca tggcttaaat ttggaagaag ctgctcggta   4320
tatgagatct ctcaaagtgc cagctacagt ttctgtttct tcacctgatg ctgttacagc   4380
gtataatggt tatcttactt cttcttctaa aacacctgaa gaacatttta ttgaaaccat   4440
ctcacttgct ggttcctata aagattggtc ctattctgga caatctacac aactaggtat   4500
agaatttctt aagagaggtg ataaaagtgt atattacact agtaatccta ccacattcca   4560
cctagatggt gaagttatca cctttgacaa tcttaagaca cttctttctt tgagagaagt   4620
gaggactatt aaggtgttta caacagtaga caacattaac ctccacacgc aagttgtgga   4680
catgtcaatg acatatggac aacagtttgg tccaacttat ttggatggag ctgatgttac   4740
taaaataaaa cctcataatt cacatgaagg taaaacattt tatgttttac ctaatgatga   4800
cactctacgt gttgaggctt ttgagtacta ccacacaact gatcctagtt ttctgggtag   4860
gtacatgtca gcattaaatc acactaaaaa gtggaaatac ccacaagtta atggtttaac   4920
ttctattaaa tgggcagata acaactgtta tcttgccact gcattgttaa cactccaaca   4980
aatagagttg aagtttaatc cacctgctct acaagatgct tattacagag caagggctgg   5040
tgaagctgct aacttttgtg cacttatctt agcctactgt aataagacag taggtgagtt   5100
aggtgatgtt agagaaacaa tgagttactt gtttcaacat gccaatttag attcttgcaa   5160
aagagtcttg aacgtggtgt gtaaaacttg tggacaacag cagacaaccc ttaagggtgt   5220
agaagctgtt atgtacatgg gcacactttc ttatgaacaa tttaagaaag gtgttcagat   5280
accttgtacg tgtggtaaac aagctacaaa atatctagta caacaggagt caccttttgt   5340
tatgatgtca gcaccacctg ctcagtatga acttaagcat ggtacattta cttgtgctag   5400
tgagtacact ggtaattacc agtgtggtca ctataaacat ataacttcta aagaaacttt   5460
gtattgcata gacggtgctt tacttacaaa gtcctcagaa tacaaaggtc ctattacgga   5520
tgttttctac aaagaaaaca gttacacaac aaccataaaa ccagttactt ataaattgga   5580
tggtgttgtt tgtacagaaa ttgaccctaa gttggacaat tattataaga aagacaattc   5640
ttatttcaca gagcaaccaa ttgatcttgt accaaaccaa ccatatccaa acgcaagctt   5700
cgataatttt aagtttgtat gtgataatat caaatttgct gatgatttaa accagttaac   5760
tggttataag aaacctgctt caagagagct taaagttaca tttttccctg acttaaatgg   5820
tgatgtggtg gctattgatt ataaacacta cacaccctct tttaagaaag gagctaaatt   5880
gttacataaa cctattgttt ggcatgttaa caatgcaact aataaagcca cgtataaacc   5940
aaatacctgg tgtatacgtt gtctttggag cacaaaacca gttgaaacat caaattcgtt   6000
tgatgtactg aagtcagagg acgcgcaggg aatggataat cttgcctgcg aagatctaaa   6060
accagtctct gaagaagtag tggaaaatcc taccatacag aaagacgttc ttgagtgtaa   6120
tgtgaaaact gatctaatgg ctgcttatgt agacaattct agtcttacta ttaagaaacc   6180
taatgaatta tctagagtat taggtttgaa aacccttgct actcatggtt tagctgctgt   6240
```

-continued taatagtgtc ccttgggata ctatagctaa ttatgctaag ccttttctta acaaagttgt 6300
tagtacaact actaacatag ttacacggtg tttaaaccgt gtttgtacta attatatgcc 6360
ttatttcttt actttattgc tacaattgtg tacttttact agaagtacaa attctagaat 6420
taaagcatct atgccgacta ctatagcaaa gaatactgtt aagagtgtcg gtaaattttg 6480
tctagaggct tcatttaatt atttgaagtc acctaatttt tctaaactga taaatattat 6540
aatttggttt ttactattaa gtgtttgcct aggttcttta atctactcaa ccgctgcttt 6600
aggtgtttta atgtctaatt taggcatgcc ttcttactgt actggttaca gagaaggcta 6660
tttgaactct actaatgtca ctattgcaac ctactgtact ggttctatac cttgtagtgt 6720
ttgtcttagt ggtttagatt ctttagacac ctatccttct ttagaaacta tacaaattac 6780
catttcatct tttaaatggg atttaactgc ttttggctta gttgcagagt ggtttttggc 6840
atatattctt ttcactaggt ttttctatgt acttggattg gctgcaatca tgcaattgtt 6900
tttcagctat tttgcagtac attttattag taattcttgg cttatgtggt taataattaa 6960
tcttgtacaa atggccccga tttcagctat ggttagaatg tacatcttct ttgcatcatt 7020
ttattatgta tggaaaagtt atgtgcatgt tgtagacggt tgtaattcat caacttgtat 7080
gatgtgttac aaacgtaata gagcaacaag agtcgaatgt acaactattg ttaatggtgt 7140
tagaaggtcc ttttatgtct atgctaatgg aggtaaaggc ttttgcaaac tacacaattg 7200
gaattgtgtt aattgtgata cattctgtgc tggtagtaca tttattagtg atgaagttgc 7260
gagagacttg tcactacagt ttaaaagacc aataaatcct actgaccagt cttcttacat 7320
cgttgatagt gttacagtga agaatggttc catccatctt tactttgata aagctggtca 7380
aaagacttat gaaagacatt ctctctctca ttttgttaac ttagacaacc tgagagctaa 7440
taacactaaa ggttcattgc ctattaatgt tatagttttt gatggtaaat caaaatgtga 7500
agaatcatct gcaaaatcag cgtctgttta ctacagtcag cttatgtgtc aacctatact 7560
gttactagat caggcattag tgtctgatgt tggtgatagt gcggaagttg cagttaaaat 7620
gtttgatgct tacgttaata cgttttcatc aacttttaac gtaccaatgg aaaaactcaa 7680
aacactagtt gcaactgcag aagctgaact tgcaaagaat gtgtccttag acaatgtctt 7740
atctactttt atttcagcag ctcggcaagg gtttgttgat tcagatgtag aaactaaaga 7800
tgttgttgaa tgtcttaaat tgtcacatca atctgacata gaagttactg gcgatagttg 7860
taataactat atgctcacct ataacaaagt tgaaaacatg acaccccgtg accttggtgc 7920
ttgtattgac tgtagtgcgc gtcatattaa tgcgcaggta gcaaaaagtc acaacattgc 7980
tttgatatgg aacgttaaag atttcatgtc attgtctgaa caactacgaa aacaaatacg 8040
tagtgctgct aaaaagaata acttaccttt taagttgaca tgtgcaacta ctagacaagt 8100
tgttaatgtt gtaacaacaa agatagcact taagggtggt aaaattgtta ataattggtt 8160
gaagcagtta attaaagtta cacttgtgtt cctttttgtt gctgctattt tctatttaat 8220
aacacctgtt catgtcatgt ctaaacatac tgacttttca agtgaaatca taggatacaa 8280
ggctattgat ggtggtgtca ctcgtgacat agcatctaca gatacttgtt ttgctaacaa 8340
acatgctgat tttgacacat ggtttagcca gcgtggtggt agttatacta atgacaaagc 8400
ttgcccattg attgctgcag tcataacaag agaagtgggt tttgtcgtgc ctggtttgcc 8460
tggcacgata ttacgcacaa ctaatggtga ctttttgcat ttcttaccta gagtttttag 8520
tgcagttggt aacatctgtt acacaccatc aaaacttata gagtacactg actttgcaac 8580
atcagcttgt gttttggctg ctgaatgtac aatttttaaa gatgcttctg gtaagccagt 8640

-continued

```
accatattgt tatgatacca atgtactaga aggttctgtt gcttatgaaa gtttacgccc   8700
tgacacacgt tatgtgctca tggatggctc tattattcaa tttcctaaca cctaccttga   8760
aggttctgtt agagtggtaa caacttttga ttctgagtac tgtaggcacg gcacttgtga   8820
aagatcagaa gctggtgttt gtgtatctac tagtggtaga tgggtactta acaatgatta   8880
ttacagatct ttaccaggag ttttctgtgg tgtagatgct gtaaatttac ttactaatat   8940
gtttacacca ctaattcaac ctattggtgc tttggacata tcagcatcta tagtagctgg   9000
tggtattgta gctatcgtag taacatgcct tgcctactat tttatgaggt ttagaagagc   9060
ttttggtgaa tacagtcatg tagttgcctt taatacttta ctattcctta tgtcattcac   9120
tgtactctgt ttaacaccag tttactcatt cttacctggt gtttattctg ttatttactt   9180
gtacttgaca ttttatctta ctaatgatgt ttcttttttta gcacatattc agtggatggt   9240
tatgttcaca cctttagtac ctttctggat aacaattgct tatatcattt gtatttccac   9300
aaagcatttc tattggttct ttagtaatta cctaaagaga cgtgtagtct ttaatggtgt   9360
ttcctttagt acttttgaag aagctgcgct gtgcaccttt ttgttaaata aagaaatgta   9420
tctaaagttg cgtagtgatg tgctattacc tcttacgcaa tataatagat acttagctct   9480
ttataataag tacaagtatt ttagtggagc aatggataca actagctaca gagaagctgc   9540
ttgttgtcat ctcgcaaagg ctctcaatga cttcagtaac tcaggttctg atgttcttta   9600
ccaaccacca caaacctcta tcacctcagc tgttttgcag agtggtttta gaaaaatggc   9660
attcccatct ggtaaagttg agggttgtat ggtacaagta acttgtggta caactacact   9720
taacggtctt tggcttgatg acgtagttta ctgtccaaga catgtgatct gcacctctga   9780
agacatgctt aaccctaatt atgaagattt actcattcgt aagtctaatc ataatttctt   9840
ggtacaggct ggtaatgttc aactcagggt tattggacat tctatgcaaa attgtgtact   9900
taagcttaag gttgatacag ccaatcctaa gacacctaag tataagtttg ttcgcattca   9960
accaggacag actttttcag tgttagcttg ttacaatggt tcaccatctg gtgtttacca  10020
atgtgctatg aggcccaatt tcactattaa gggttcattc cttaatggtt catgtggtag  10080
tgttggtttt aacatagatt atgactgtgt ctctttttgt tacatgcacc atatggaatt  10140
accaactgga gttcatgctg gcacagactt agaaggtaac ttttatggac cttttgttga  10200
caggcaaaca gcacaagcag ctggtacgga cacaactatt acagttaatg ttttagcttg  10260
gttgtacgct gctgttataa atggagacag gtggtttctc aatcgattta ccacaactct  10320
taatgacttt aaccttgtgg ctatgaagta caattatgaa cctctaacac aagaccatgt  10380
tgacatacta ggacctcttt ctgctcaaac tggaattgcc gttttagata tgtgtgcttc  10440
attaaaagaa ttactgcaaa atggtatgaa tggacgtacc atattgggta gtgctttatt  10500
agaagatgaa tttacacctt ttgatgttgt tagacaatgc tcaggtgtta ctttccaaag  10560
tgcagtgaaa agaacaatca agggtacaca ccactggttg ttactcacaa ttttgacttc  10620
acttttagtt ttagtccaga gtactcaatg gtctttgttc tttttttttgt atgaaaatgc  10680
ctttttacct tttgctatgg gtattattgc tatgtctgct tttgcaatga tgtttgtcaa  10740
acataagcat gcatttctct gtttgttttt gttaccttct cttgccactg tagcttattt  10800
taatatggtc tatatgcctg ctagttgggt gatgcgtatt atgacatggt tggatatggt  10860
tgatactagt ttgtctggtt ttaagctaaa agactgtgtt atgtatgcat cagctgtagt  10920
gttactaatc cttatgacag caagaactgt gtatgatgat ggtgctagga gagtgtggac  10980
```

-continued

```
acttatgaat gtcttgacac tcgtttataa agtttattat ggtaatgctt tagatcaagc  11040
catttccatg tgggctctta taatctctgt tacttctaac tactcaggtg tagttacaac  11100
tgtcatgttt ttggccagag gtattgtttt tatgtgtgtt gagtattgcc ctattttctt  11160
cataactggt aatacacttc agtgtataat gctagtttat tgtttcttag gctatttttg  11220
tacttgttac tttggcctct tttgtttact caaccgctac tttagactga ctcttggtgt  11280
ttatgattac ttagtttcta cacaagagtt tagatatatg aattcacagg gactactccc  11340
acccaagaat agcatagatg ccttcaaact caacattaaa ttgttgggtg ttggtggcaa  11400
accttgtatc aaagtagcca ctgtacagtc taaaatgtca gatgtaaagt gcacatcagt  11460
agtcttactc tcagttttgc aacaactcag agtagaatca tcatctaaat tgtgggctca  11520
atgtgtccag ttacacaatg acattctctt agctaaagat actactgaag cctttgaaaa  11580
aatggtttca ctactttctg ttttgctttc catgcagggt gctgtagaca taaacaagct  11640
ttgtgaagaa atgctggaca acagggcaac cttacaagct atagcctcag agtttagttc  11700
ccttccatca tatgcagctt ttgctactgc tcaagaagct tatgagcagg ctgttgctaa  11760
tggtgattct gaagttgttc ttaaaaagtt gaagaagtct ttgaatgtgg ctaaatctga  11820
atttgaccgt gatgcagcca tgcaacgtaa gttggaaaag atggctgatc aagctatgac  11880
ccaaatgtat aaacaggcta gatctgagga caagagggca aaagttacta gtgctatgca  11940
gacaatgctt ttcactatgc ttagaaagtt ggataatgat gcactcaaca acattatcaa  12000
caatgcaaga gatggttgtg ttcccttgaa cataatacct cttacaacag cagccaaact  12060
aatggttgtc ataccagact ataacacata taaaaatacg tgtgatggta caacatttac  12120
ttatgcatca gcattgtggg aaatccaaca ggttgtagat gcagatagta aaattgttca  12180
acttagtgaa attagtatgg acaattcacc taatttagca tggcctctta ttgtaacagc  12240
tttaagggcc aattctgctg tcaaattaca gaataatgag cttagtcctg ttgcactacg  12300
acagatgtct tgtgctgccg gtactacaca aactgcttgc actgatgaca atgcgttagc  12360
ttactacaac acaacaaagg gaggtaggtt tgtacttgca ctgttatccg atttacagga  12420
tttgaaatgg gctagattcc ctaagagtga tggaactggt actatctata cagaactggt  12480
acttggtagt ttagctgcca cagtacgtct acaagctggt aatgcaacag aagtgcctgc  12540
caattcaact gtattatctt tctgtgcttt tgctgtagat gctgctaaag cttacaaaga  12600
ttatctagct agtgggggac aaccaatcac taattgtgtt aagatgttgt gtacacacac  12660
tggtactggt caggcaataa cagttacacc ggaagccaat atggatcaag aatcctttgg  12720
tggtgcatcg tgttgtctgt actgccgttg ccacatagat catccaaatc ctaaaggatt  12780
ttgtgactta aaaggtaagt atgtacaaat acctacaact tgtgctaatg accctgtggg  12840
ttttacactt aaaaacacag tctgtaccgt ctgcggtatg tggaaaggtt atggctgtag  12900
ttgtgatcaa ctccgcgaac ccatgcttca gtcagctgat gcacaatcgt tttaaacgg  12960
gtttgcggtg taagtgcagc ccgtcttaca ccgtgcggca caggcactag tactgatgtc  13020
gtatacaggg cttttgacat ctacaatgat aaagtagctg gttttgctaa attcctaaaa  13080
actaattgtt gtcgcttcca agaaaaggac gaagatgaca atttaattga ttcttacttt  13140
gtagttaaga gacacacttt ctctaactac caacatgaag aaacaattta taatttactt  13200
aaggattgtc cagctgttgc taaacatgac ttctttaagt ttagaataga cggtgacatg  13260
gtaccacata tatcacgtca acgtcttact aaatacacaa tggcagacct cgtctatgct  13320
ttaaggcatt ttgatgaagg taattgtgac acattaaaag aaatacttgt cacatacaat  13380
```

```
tgttgtgatg atgattattt caataaaaag gactggtatg attttgtaga aaacccagat  13440
atattacgcg tatacgccaa cttaggtgaa cgtgtacgcc aagctttgtt aaaaacagta  13500
caattctgtg atgccatgcg aaatgctggt attgttggtg tactgacatt agataatcaa  13560
gatctcaatg gtaactgatg cctatattaa ccttgaccag ggctttaact gcagagtcac  13620
atgttgacac tgacttaaca aagccttaca ttaagtggga tttgttaaaa tatgacttca  13680
cggaagagag gttaaaactc tttgaccgtt attttaaata ttgggatcag acataccacc  13740
caaattgtgt taactgtttg gatgacagat gcattctgca ttgtgcaaac tttaatgttt  13800
tattctctac agtgttccca cttacaagtt ttggaccact agtgagaaaa atatttgttg  13860
atggtgttcc atttgtagtt tcaactggat accacttcag agagctaggt gttgtacata  13920
atcaggatgt aaacttacat agctctagac ttagttttaa ggaattactt gtgtatgctg  13980
ctgaccctgc tatgcacgct gcttctggta atctattact agataaacgc actacgtgct  14040
tttcagtagc tgcacttact aacaatgttg cttttcaaac tgtcaaaccc ggtaatttta  14100
acaaagactt ctatgacttt gctgtgtcta agggtttctt taaggaagga agttctgttg  14160
aattaaaaca cttcttcttt gctcaggatg gtaatgctgc tatcagcgat tatgactact  14220
atcgttataa tctaccaaca atgtgtgata tcagacaact actatttgta gttgaagttg  14280
ttgataagta ctttgattgt tacgatggtg gctgtattaa tgctaaccaa gtcatcgtca  14340
acaacctaga caaatcagct ggttttccat ttaataaatg ggtaaggct agactttatt  14400
atgattcaat gagttatgag gatcaagatg cacttttcgc atatacaaaa cgtaatgtca  14460
tccctactat aactcaaatg aatcttaagt atgccattag tgcaaagaat agagctcgca  14520
ccgtagctgg tgtctctatc tgtagtacta tgaccaatag acagtttcat caaaaattat  14580
tgaaatcaat agccgccact agaggagcta ctgtagtaat tggaacaagc aaattctatg  14640
gtggttggca caacatgtta aaaactgttt atagtgatgt agaaaaccct caccttatgg  14700
gttgggatta tcctaaatgt gatagagcca tgcctaacat gcttagaatt atggcctcac  14760
ttgttcttgc tcgcaaacat acaacgtgtt gtagcttgtc acaccgtttc tatagattag  14820
ctaatgagtg tgctcaagta ttgagtgaaa tggtcatgtg tggcggttca ctatatgtta  14880
aaccaggtgg aacctcatca ggagatgcca caactgctta tgctaatagt gtttttaaca  14940
tttgtcaagc tgtcacggcc aatgttaatg cacttttatc tactgatggt aacaaaattg  15000
ccgataagta tgtccgcaat ttacaacaca gactttatga gtgtctctat agaaatagag  15060
atgttgacac agactttgtg aatgagtttt acgcatattt gcgtaaacat ttctcaatga  15120
tgatactctc tgacgatgct gttgtgtgtt tcaatagcac ttatgcatct caaggtctag  15180
tggctagcat aaagaacttt aagtcagttc tttattatca aaacaatgtt tttatgtctg  15240
aagcaaaatg ttggactgag actgacctta ctaaaggacc tcatgaattt tgctctcaac  15300
atacaatgct agttaaacag ggtgatgatt atgtgtacct tccttaccca gatccatcaa  15360
gaatcctagg ggccggctgt tttgtagatg atatcgtaaa aacagatggt acacttatga  15420
ttgaacggtt cgtgtcttta gctatagatg cttacccact tactaaacat cctaatcagg  15480
agtatgctga tgtctttcat ttgtacttac aatacataag aaagctacat gatgagttaa  15540
caggacacat gttagacatg tattctgtta tgcttactaa tgataacact tcaaggtatt  15600
gggaacctga gttttatgag gctatgtaca caccgcatac agtcttacag gctgttgggg  15660
cttgtgttct ttgcaattca cagacttcat taagatgtgg tgcttgcata cgtagaccat  15720
```

-continued

```
tcttatgttg taaatgctgt tacgaccatg tcatatcaac atcacataaa ttagtcttgt  15780
ctgttaatcc gtatgtttgc aatgctccag gttgtgatgt cacagatgtg actcaacttt  15840
acttaggagg tatgagctat tattgtaaat cacataaacc acccattagt tttccattgt  15900
gtgctaatgg acaagttttt ggtttatata aaaatacatg tgttggtagc gataatgtta  15960
ctgactttaa tgcaattgca acatgtgact ggacaaatgc tggtgattac attttagcta  16020
acacctgtac tgaaagactc aagctttttg cagcagaaac gctcaaagct actgaggaga  16080
catttaaact gtcttatggt attgctactg tacgtgaagt gctgtctgac agagaattac  16140
atctttcatg ggaagttggt aaacctagac caccacttaa ccgaaattat gtctttactg  16200
gttatcgtgt aactaaaaac agtaaagtac aaataggaga gtacaccttt gaaaaaggtg  16260
actatggtga tgctgttgtt taccgaggta caacaactta caaattaaat gttggtgatt  16320
attttgtgct gacatcacat acagtaatgc cattaagtgc acctacacta gtgccacaag  16380
agcactatgt tagaattact ggcttatacc caacactcaa tatctcagat gagttttcta  16440
gcaatgttgc aaattatcaa aaggttggta tgcaaaagta ttctacactc cagggaccac  16500
ctggtactgg taagagtcat tttgctattg gcctagctct ctactaccct tctgctcgca  16560
tagtgtatac agcttgctct catgccgctg ttgatgcact atgtgagaag gcattaaaat  16620
atttgcctat agataaatgt agtagaatta tacctgcacg tgctcgtgta gagtgttttg  16680
ataaattcaa agtgaattca acattagaac agtatgtctt ttgtactgta aatgcattgc  16740
ctgagacgac agcagatata gttgtctttg atgaaatttc aatggccaca aattatgatt  16800
tgagtgttgt caatgccaga ttacgtgcta agcactatgt gtacattggc gaccctgctc  16860
aattacctgc accacgcaca ttgctaacta agggcacact agaaccagaa tatttcaatt  16920
cagtgtgtag acttatgaaa actataggtc cagacatgtt cctcggaact tgtcggcgtt  16980
gtcctgctga aattgttgac actgtgagtg ctttggttta tgataataag cttaaagcac  17040
ataaagacaa atcagctcaa tgctttaaaa tgttttataa gggtgttatc acgcatgatg  17100
tttcatctgc aattaacagg ccacaaatag gcgtggtaag agaattcctt acacgtaacc  17160
ctgcttggag aaaagctgtc tttatttcac cttataattc acagaatgct gtagcctcaa  17220
agattttggg actaccaact caaactgttg attcatcaca gggctcagaa tatgactatg  17280
tcatattcac tcaaaccact gaaacagctc actcttgtaa tgtaaacaga tttaatgttg  17340
ctattaccag agcaaaagta ggcatacttt gcataatgtc tgatagagac ctttatgaca  17400
agttgcaatt tacaagtctt gaaattccac gtaggaatgt ggcaacttta caagctgaaa  17460
atgtaacagg actctttaaa gattgtagta aggtaatcac tgggttacat cctacacagg  17520
cacctacaca cctcagtgtt gacactaaat tcaaaactga aggtttatgt gttgacatac  17580
ctggcatacc taaggacatg acctatagaa gactcatctc tatgatgggt tttaaaatga  17640
attatcaagt taatggttac cctaacatgt ttatcacccg cgaagaagct ataagacatg  17700
tacgtgcatg gattggcttc gatgtcgagg ggtgtcatgc tactagagaa gctgttggta  17760
ccaatttacc tttacagcta ggtttttcta caggtgttaa cctagttgct gtacctacag  17820
gttatgttga tacacctaat aatacagatt tttccagagt tagtgctaaa ccaccgcctg  17880
gagatcaatt taaacacctc ataccactta tgtacaaagg acttccttgg aatgtagtgc  17940
gtataaagat tgtacaaatg ttaagtgaca cacttaaaaa tctctctgac agagtcgtat  18000
ttgtcttatg ggcacatggc tttgagttga catctatgaa gtattttgtg aaaataggac  18060
ctgagcgcac ctgttgtcta tgtgatagac gtgccacatg cttttccact gcttcagaca  18120
```

```
cttatgcctg ttggcatcat tctattggat ttgattacgt ctataatccg tttatgattg  18180
atgttcaaca atggggtttt acaggtaacc tacaaagcaa ccatgatctg tattgtcaag  18240
tccatggtaa tgcacatgta gctagttgtg atgcaatcat gactaggtgt ctagctgtcc  18300
acgagtgctt tgttaagcgt gttgactgga ctattgaata tcctataatt ggtgatgaac  18360
tgaagattaa tgcggcttgt agaaaggttc aacacatggt tgttaaagct gcattattag  18420
cagacaaatt cccagttctt cacgacattg gtaaccctaa agctattaag tgtgtacctc  18480
aagctgatgt agaatggaag ttctatgatg cacagccttg tagtgacaaa gcttataaaa  18540
tagaagaatt attctattct tatgccacac attctgacaa attcacagat ggtgtatgcc  18600
tattttggaa ttgcaatgtc gatagatatc ctgctaattc cattgtttgt agatttgaca  18660
ctagagtgct atctaacctt aacttgcctg gttgtgatgg tggcagtttg tatgtaaata  18720
aacatgcatt ccacacacca gcttttgata aaagtgcttt tgttaattta aaacaattac  18780
catttttcta ttactctgac agtccatgtg agtctcatgg aaaacaagta gtgtcagata  18840
tagattatgt accactaaag tctgctacgt gtataacacg ttgcaattta ggtggtgctg  18900
tctgtagaca tcatgctaat gagtacagat tgtatctcga tgcttataac atgatgatct  18960
cagctggctt tagcttgtgg gtttacaaac aatttgatac ttataacctc tggaacactt  19020
ttacaagact tcagagttta gaaaatgtgg cttttaatgt tgtaaataag ggacactttg  19080
atggacaaca gggtgaagta ccagtttcta tcattaataa cactgtttac acaaaagttg  19140
atggtgttga tgtagaattg tttgaaaata aaacaacatt acctgttaat gtagcatttg  19200
agctttgggc taagcgcaac attaaaccag taccagaggt gaaaatactc aataatttgg  19260
gtgtggacat tgctgctaat actgtgatct gggactacaa aagagatgct ccagcacata  19320
tatctactat tggtgtttgt tctatgactg acatagccaa gaaaccaact gaaacgattt  19380
gtgcaccact cactgtcttt tttgatggta gagttgatgg tcaagtagac ttatttagaa  19440
atgcccgtaa tggtgttctt attacagaag gtagtgttaa aggtttacaa ccatctgtag  19500
gtcccaaaca agctagtctt aatggagtca cattaattgg agaagccgta aaaacacagt  19560
tcaattatta taagaaagtt gatggtgttg tccaacaatt acctgaaact tactttactc  19620
agagtagaaa tttacaagaa tttaaaccca ggagtcaaat ggaaattgat ttcttagaat  19680
tagctatgga tgaattcatt gaacggtata aattagaagg ctatgccttc gaacatatcg  19740
tttatggaga ttttagtcat agtcagttag gtggtttaca tctactgatt ggactagcta  19800
aacgttttaa ggaatcacct tttgaattag aagattttat tcctatggac agtacagtta  19860
aaaactattt cataacagat gcgcaaacag ggtcaaagtg actattgact atacagaaat  19920
ttcatttatg ctttggtgta aagatggcca tgtagaaaca ttttacccaa aattacaatc  19980
tagtcaagcg tggcaaccgg gtgttgctat gcctaatctt tacaaaatgc aaagaatgct  20040
attagaaaag tgtgaccttc aaaattatgg tgatagtgca acattaccta aaggcataat  20100
gatgaatgtc gcaaaatata ctcaactgtg tcaatattta aacacattaa cattagctgt  20160
accctataat atgagagtta tacattttgg tgctggttct gataaaggag ttgcaccagg  20220
tacagctgtt ttaagacagt ggttgcctac gggtacgctg cttgtcgatt cagatcttaa  20280
tgactttgtc tctgatgcag attcaacttt gattggtgat tgtgcaactg tacatacagc  20340
taataaatgg gatctcatta ttagtgatat gtacgaccct aagactaaaa atgttacaaa  20400
agaaaatgac tctaaagagg gtttttttcac ttacatttgt gggtttatac aacaaaagct  20460
```

-continued

```
agctcttgga ggttccgtgg ctataaagat aacagaacat tcttggaatg ctgatcttta  20520
taagctcatg ggacacttcg catggtggac agcctttgtt actaatgtga atgcgtcatc  20580
atctgaagca tttttaattg gatgtaatta tcttggcaaa ccacgcgaac aaatagatgg  20640
ttatgtcatg catgcaaatt acatattttg gaggaataca aatccaattc agttgtcttc  20700
ctattcttta tttgacatga gtaaatttcc ccttaaatta aggggtactg ctgttatgtc  20760
tttaaaagaa ggtcaaatca atgatatgat tttatctctt cttagtaaag gtagacttat  20820
aattagagaa aacaacagag ttgttatttc tagtgatgtt cttgttaaca actaaacgaa  20880
caatgtttgt ttttcttgtt ttattgccac tagtctctag tcagtgtgtt aatcttacaa  20940
ccagaactca attaccccct gcatacacta attctttcac acgtggtgtt tattaccctg  21000
acaaagtttt cagatcctca gttttacatt caactcagga cttgttctta cctttctttt  21060
ccaatgttac ttggttccat gctatacatg tctctgggac caatggtact aagaggtttg  21120
ataaccctgt cctaccattt aatgatggtg tttattttgc ttccactgag aagtctaaca  21180
taataagagg ctggattttt ggtactactt tagattcgaa gacccagtcc ctacttattg  21240
ttaataacgc tactaatgtt gttattaaag tctgtgaatt tcaattttgt aatgatccat  21300
ttttgggtgt ttattaccac aaaaacaaca aaagttggat ggaaagtgag ttcagagttt  21360
attctagtgc gaataattgc acttttgaat atgtctctca gccttttctt atggaccttg  21420
aaggaaaaca gggtaatttc aaaaatcgat ctccctcagg gtttttcggc tttagaacca  21480
ttggtagatt tgccaatagg tattaacatc actaggtttc aaactttact tgctttacat  21540
agaagttatt tgactcctgg tgattcttct tcaggttgga cagctggtgc tgcagcttat  21600
tatgtgggtt atcttcaacc taggactttt ctattaaaat ataatgaaaa tggaaccatt  21660
acagatgctg tagactgtgc acttgaccct ctctcagaaa caaagtgtac gttgaaatcc  21720
ttcactgtag aaaaaggaat ctatcaaact tctaacttta gagtctgcat ctgtttatgc  21780
ttggaacagg aagagaatca gcaactgtgt tgctgattat tctgtcctat ataattccgc  21840
atcattttcc acttttaagt gttatggagt gtctcctact aaattaaatg atctctgctt  21900
tactaatgtc tatgcagatt catttgtaat tagaggtgat gaagtcagac aaatcgctcc  21960
agggcaaact ggaaagattg ctgattataa ttataaatta ccagatgatt ttacaggctg  22020
cgttatagct tggaattcta acaatcttga ttctaaggtt ggtggtaatt ataattacct  22080
gtatagattg tttaggaagt ctaatctcaa accttttgag agagatattt caactgaaat  22140
ctatcaggcc ggtagcacac cttgtaatgg tgttgaaggt gtactttctt ttgaacttct  22200
acatgcacca gcaactgttt gtggacctaa aaagtctact aatttggtta aaaacaaatg  22260
tgtcaatttc aacttcaatg gtttaacagg cacaggtgtt cttactgagt ctaacaaaaa  22320
gtttctgcct ttccaacaat ttggcagaga cattgctgac actactgatg ctgtccgtga  22380
tccacagaca cttgagattc ttgacattac accatgttct tttggtggtg tcagtgttat  22440
aacaccagga acaaatactt ctaaccaggt tgctgttctt tatcagggtg ttaactgcac  22500
agaagtccct gttgctattc atgcagatca acttactcct acttggcgtg tttattctac  22560
aggttctaat gtttttcaaa cacgtgcagg ctgtttaata ggggctgaac atgtcaacaa  22620
ctcatatgag tgtgacatac ccattggtgc aggtatatgc gctagttatc agactcagac  22680
taattctcct cggcgggcac gtagtgtagc tagtcaatcc atcattgcct acactatgtc  22740
acttggtgca gaaaattcag ttgcttactc taataactct attgccatac ccacaaattt  22800
tactattagt gttaccacag aaattctacc agtgtctatg accaagacat cagtagattg  22860
```

-continued

```
tacaatgtac atttgtggtg attcaactga atgcagcaat cttttgttgc aatatggcag  22920
tttttgtaca caattaaacc gtgctttaac tggaatagct gttgaacaag acaaaaacac  22980
ccaagaagtt tttgcacaag tcaaacaaat ttacaaaaca ccaccaatta aagattttgg  23040
tggttttaat ttttcacaaa tattaccaga tccatcaaaa ccaagcaaga ggtcatttat  23100
tgaagatcta cttttcaaca aagtgacact tgcagatgct ggcttcatca aacaatatgg  23160
tgattgcctt ggtgatattg ctgctagaga cctcatttgt gcacaaaagt ttaacggcct  23220
tactgttttg ccacctttgc tcacagatga aatgattgct caatacactt ctgcactgtt  23280
agcgggtaca atcacttctg gttggacctt tggtgcaggt gctgcattac aaataccatt  23340
tgctatgcgc tattggcaaa attcaagact cactttcttc cacagcaagt gcacttggaa  23400
aacttcaaga tgtggtcaac caaaatgcac aagctttaaa cacgcttgtt aaacaactta  23460
gctccaattt tggtgcaatt tcaagtgttt taaatgatat cctttcacgt cttgacaaag  23520
ttgaggctga agtgcaaatt gataggttga tcacaggcag acttcaaagt ttgcagacat  23580
atgtgactca acaattaatt agagctgcag aaatcagagc ttctgctaat cttgctgcta  23640
ctaaaatgtc agagtgtgta cttggacaat caaaaagagt tgatttttgt ggaaagggct  23700
atcatcttat gtccttccct cagtcagcac ctcatggtgt agtcttcttg catgtgactt  23760
atgtccctgc acaagaaaag aacttcacaa ctgctcctgc catttgtcat gatggaaaag  23820
cacactttcc tcgtgaaggt gtctttgttt caaatggcac acactggttt gtaacacaaa  23880
ggaattttta tgaaccacaa atcattacta cagacaacac atttgtgtct ggtaactgtg  23940
atgttgtaat aggaattgtc aacaacacag tttatgatcc tttgcaacct gaattagact  24000
cattcaagga ggagttagat aaatatttta agaatcatac atcaccagat gttgatttag  24060
gtgacatctc tggcattaat gcttcagttg taaacattca aaaagaaatt gaccgcctca  24120
atgaggttgc caagaattta aatgaatctc tcatcgatct ccaagaactt ggaaagtatg  24180
agcagtatat aaaatggcca tggtacattt ggctaggttt tatagctggc ttgattgcca  24240
tagtaatggt gacaattatg ctttgctgta tgaccagttg ctgtagttgt ctcaagggct  24300
gttgttcttg tggatcctgc tgcaaatttg atgaagacga ctctgagcca gtgctcaaag  24360
gagtcaaatt acattacaca taaacgaact tatggatttg tttatgagaa tcttcacaat  24420
tggaactgta actttgaagc aaggtgaaat caaggatgct actccttcag attttgttcg  24480
cgctactgca acgataccga tacaagcctc actccctttc ggatggctta ttgttggcgt  24540
tgcacttctt gctgtttttc agagcgcttc caaaatcata accctcaaaa agagatggca  24600
actagcactc tccaagggtg ttcactttgt ttgcaacttg ctgttgttgt ttgtaacagt  24660
ttactcacac cttttgctcg ttgctgctgg ccttgaagcc ccttttctct atctttatgc  24720
tttagtctac ttcttgcaga gtataaactt tgtaagaata ataatgaggc tttggctttg  24780
ctggaaatgc cgttccaaaa acccattact ttatgatgcc aactattttc tttgctggca  24840
tactaattgt tacgactatt gtatacctta caatagtgta acttcttcaa ttgtcattac  24900
ttcaggtgat ggcacaacaa gtcctatttc tgaacatgac taccagattg gtggttatac  24960
tgaaaaatgg gaatctggag taaaagactg tgttgtatta cacagttact tcacttcaga  25020
ctattaccag ctgtactcaa ctcaattgag tacagacact ggtgttgaac atgttacctt  25080
cttcatctac aataaaattg ttgatgagcc tgaagaacat gtccaaattc acacaatcga  25140
cggttcatcc ggagttgtta atccagtaat ggaaccaatt tatgatgaac cgacgacgac  25200
```

-continued

```
tactagcgtg cctttgtaag cacaagctga tgagtacgaa cttatgtact cattcgtttc  25260
ggaagagaca ggtacgttaa tagttaatag cgtacttctt tttcttgctt tcgtggtatt  25320
cttgctagtt acactagcca tccttactgc gcttcgattg tgtgcgtact gctgcaatat  25380
tgttaacgtg agtcttgtaa aaccttcttt ttacgtttac tctcgtgtta aaaatctgaa  25440
ttcttctaga gttcctgatc ttctggtcta aacgaactaa atattatatt agtttttctg  25500
tttggaactt taattttagc catggcagat tccaacggta ctattaccgt tgaagagctt  25560
aaaaagctcc ttgaacaatg gaacctagta ataggtttcc tattccttac atggatttgt  25620
cttctacaat ttgcctatgc caacaggaat aggtttttgt atataattaa gttaattttc  25680
ctctggctgt tatggccagt aactttagct tgttttgtgc ttgctgctgt ttacagaata  25740
aattggatca ccggtggaat tgctatcgca atggcttgtc ttgtaggctt gatgtggctc  25800
agctacttca ttgcttcttt cagactgttt gcgcgtacgc gttccatgtg gtcattcaat  25860
ccagaaacta acattcttct caacgtgcca ctccatggca ctattctgac cagaccgctt  25920
ctagaaagtg aactcgtaat cggagctgtg atccttcgtg gacatcttcg tattgctgga  25980
caccatctag gacgctgtga catcaaggac ctgcctaaag aaatcactgt tgctacatca  26040
cgaacgcttt cttattacaa attgggagct tcgcagcgtg tagcaggtga ctcaggtttt  26100
gctgcataca gtcgctacag gattggcaac tataaattaa acacagacca ttccagtagc  26160
agtgacaata ttgctttgct tgtacagtaa gtgacaacag atgtttcatc tcgttgactt  26220
tcaggttact atagcagaga tattactaat tattatgagg acttttaaag tttccatttg  26280
gaatcttgat tacatcataa acctcataat taaaaattta tctaagtcac taactgagaa  26340
taaatattct caattagatg aagagcaacc aatggagatt gattaaacga acatgaaaat  26400
tattcttttc ttggcactga taacactcgc tacttgtgag ctttatcact accaagagtg  26460
tgttagaggt acaacagtac ttttaaaaga accttgctct tctggaacat acgagggcaa  26520
ttcaccattt catcctctag ctgataacaa atttgcactg acttgcttta gcactcaatt  26580
tgcttttgct tgtcctgacg gcgtaaaaca cgtctatcag ttacgtgcca gatcagtttc  26640
acctaaactg ttcatcagac aagaggaagt tcaagaactt tactctccaa tttttcttat  26700
gacttctatt tgtgcttttt agcctttctg ctattccttg ttttaattat gcttattatc  26760
ttttggttct cacttgaact gcaagatcat aatgaaactt gtcacgccta aacgaacatg  26820
aaatttcttg ttttcttagg aatcatcaca actgtagctg catttcacca agaatgtagt  26880
ttacagtcat gtactcaaca tcaaccatat gtagttgatg acccgtgtcc tattcacttc  26940
tattctaaat ggtatattag agtaggagct agaaaatcag caccttttaat tgaattgtgc  27000
gtggatgagg ctggttctaa atcacccatt cagtacatcg atatcggtaa ttatacagtt  27060
tcctgtttac cttttacaat taattgccag gaacctaaat tgggtagtct tgtagtgcgt  27120
tgttcgttct atgaagactt tttagagtat catgacgttc gtgttgtttt agatttcatc  27180
taaacgaaca aactaaaatg tctgataatg gaccccaaaa tcagcgaaat gcaccccgca  27240
ttacgtttgg tggaccctca gattcaactg gcagtaacca gaatggagaa cgcagtgggg  27300
cgcgatcaaa acaacgtcgg ccccaaggtt tacccaataa tactgcgtct tggttcaccg  27360
ctctcactca acatggcaag gaagacctta aattccctcg aggacaaggc gttccaatta  27420
acaccaatag cagtccagat gaccaaattg gctactaccg aagagctacc agacgaattc  27480
gtggtggtga cggtaaaatg aaagatctca gtccaagatg gtatttctac tacctaggaa  27540
ctgggccaga agctggactt ccctatggtg ctaacaaaga cggcatcata tgggttgcaa  27600
```

-continued

```
ctgagggagc cttgaataca ccaaaagatc acattggcac ccgcaatcct gctaacaatg  27660

ctgcaatcgt gctacaactt cctcaaggaa caacattgcc aaaaggcttc tacgcagaag  27720

ggagcagagg cggcagtcaa gcctcttctc gttcctcatc acgtagtcgc aacagttcaa  27780

gaaattcaac tccaggcagc agtaaacgaa cttctcctgc tagaatggct ggcaatggcg  27840

gtgatgctgc tcttgctttg ctgctgcttg acagattgaa ccagcttgag agcaaaatgt  27900

ctggtaaagg ccaacaacaa caaggccaaa ctgtcactaa gaaatctgct gctgaggctt  27960

ctaagaagcc tcggcaaaaa cgtactgcca ctaaagcata caatgtaaca caagctttcg  28020

gcagacgtgg tccagaacaa acccaaggaa attttgggga ccaggaacta atcagacaag  28080

gaactgatta caaacattgg ccgcaaattg cacaatttgc ccccagcgct tcagcgttct  28140

tcggaatgtc gcgcattggc atggaagtca caccttcggg aacgtggttg acctacacag  28200

gtgccatcaa attggatgac aaagatccaa atttcaaaga tcaagtcatt ttgctgaata  28260

agcatattga cgcatacaaa acattcccac caacagagcc taaaaaggac aaaaagaaga  28320

aggctgatga aactcaagcc ttaccgcaga gacagaagaa acagcaaact gtgactcttc  28380

ttcctgctgc agatttggat gatttctcca aacaattgca acaatccatg agcagtgctg  28440

actcaactca ggcctaaact catgcagacc acacaaggca gatgggctat ataaacgttt  28500

tcgcttttcc gtttacgata tatagtctac tcttgtgcag aatgaattct cgtaactaca  28560

tagcacaagt agatgtagtt aactttaatc tcacatagca atctttaatc agtgtgtaac  28620

attagggagg acttgaaaga gccaccacat tttcaccgag gccacgcgga gtacgatcga  28680

gtgtacagtg aacaatgcta gggagagctg cctatatgga agagccctaa tgtgtaaaat  28740

taattttagt agtgctatcc ccatgtgatt ttaatagctt cttaggagaa tgacaaaaaa  28800

aaaaaaaaaa aaaaaaaaaa aaaaaaa                                      28827
```